(12) United States Patent
Schuivens et al.

(10) Patent No.: US 9,978,289 B2
(45) Date of Patent: May 22, 2018

(54) COMMUNICATION DEVICE FOR PRIMATES, IN PARTICULAR PERSONS, AND METHOD FOR OPERATING SUCH A DEVICE

(71) Applicant: MERGENT B.V., Haarlem (NL)

(72) Inventors: Dennis Emile Armand Schuivens, Alkmaar (NL); Shih Chien Chen, Haarlem (NL)

(73) Assignee: MERGENT B.V., Haarlem (NL)

( * ) Notice: Subject to any disclaimer, the term of this patent is extended or adjusted under 35 U.S.C. 154(b) by 0 days. days.

(21) Appl. No.: 15/533,112

(22) PCT Filed: Dec. 4, 2015

(86) PCT No.: PCT/NL2015/050846
§ 371 (c)(1),
(2) Date: Jun. 5, 2017

(87) PCT Pub. No.: WO2016/089212
PCT Pub. Date: Jun. 9, 2016

(65) Prior Publication Data
US 2017/0330483 A1    Nov. 16, 2017

(30) Foreign Application Priority Data
Dec. 4, 2014  (NL) ...................................... 2013920

(51) Int. Cl.
G09B 21/00 (2006.01)
A61B 5/053 (2006.01)

(52) U.S. Cl.
CPC ............ *G09B 21/00* (2013.01); *A61B 5/0531* (2013.01); *A61B 2503/40* (2013.01);
(Continued)

(58) Field of Classification Search
CPC .... G06F 3/016; G06F 3/011; G06F 2203/014; G06F 3/0346; G06F 3/04842; G06F 3/0488; G06F 3/04883
(Continued)

(56) References Cited

U.S. PATENT DOCUMENTS

| | | | | |
|---|---|---|---|---|
| 8,920,332 B2* | 12/2014 | Hong | ................. | A61B 5/02427 600/309 |
| 8,935,119 B2* | 1/2015 | Yuen | ..................... | G01B 21/16 702/138 |

(Continued)

FOREIGN PATENT DOCUMENTS

| | | |
|---|---|---|
| EP | 0026796 A1 | 4/1981 |
| WO | 2005/018442 A1 | 3/2005 |

OTHER PUBLICATIONS

International Search Report dated May 31, 2016 in corresponding Application No. PCT/NL2015/050846; 4 pgs.
(Continued)

*Primary Examiner* — Mark Blouin
(74) *Attorney, Agent, or Firm* — Maier & Maier, PLLC

(57) ABSTRACT

Communication device for primates, in particular persons, including at least one electrically conductive first surface to be touched by a first primate, at least one electrically conductive second surface to be touched by at least one second primate, and at least primary electronic circuit electrically connecting said first surface and said second, said primary electronic circuit having: at least one detection element for measuring at least one resistance value of a secondary electronic circuit formed by at least the primary electronic circuit, a first primate touching said first surface, at least one second primate touching said second surface, and the first primate and the other least second primate touching each other, and at least one output for producing a
(Continued)

specific signal representing the specific resistance value detected by said at least one detection element.

20 Claims, 10 Drawing Sheets

(52) U.S. Cl.
CPC ............... *A61B 2560/0425* (2013.01); *A61B 2562/0214* (2013.01); *A61B 2562/04* (2013.01)

(58) Field of Classification Search
USPC ........................................................ 340/4.12
See application file for complete search history.

(56) References Cited

U.S. PATENT DOCUMENTS

| | | | |
|---|---|---|---|
| 8,945,017 B2* | 2/2015 | Venkatraman | A61B 5/721 600/500 |
| 9,060,700 B2* | 6/2015 | Cho | A61B 5/01 |
| 9,364,158 B2* | 6/2016 | Banet | A61B 5/01 |
| 9,410,979 B2* | 8/2016 | Yuen | G01P 7/00 |
| 2008/0139957 A1 | 6/2008 | Hubbard et al. | |

OTHER PUBLICATIONS

International Preliminary Report on Patentability in corresponding Application No. PCT/NL2015/050846; 40 pgs.

Search Report dated May 21, 2015 in corresponding Application No. NL 2013920; 10 pgs.

Hank Levin: "Virtual Clarity Meter Owner's Manual", 2010, pp. 1-15, XP002757707, Retrieved from the Internet: URL: http://clearingtech.net/downloads/VCM.OwnersManual8.9.11.pdf, retrieved on May 13, 2016, 15 pgs.

Theta-Meter: "Theta-Meter program installation and review", Aug. 20, 2013 (Aug. 20, 2013), XP054975870, Youtube Retrieved from the Internet: URL:https://www.youtube.com/watch?v=gDo0Pmtpco0, retrieved on May 21, 2015.

Hank Levin: "Virtual Clarity Meter", Jan. 21, 2011 (Jan. 21, 2011), XP002739887, Retrieved from the Internet: URL: http://clearingtech.net/2011/01/virtualclaritymeter/, retrieved on May 20, 2015, 2 pgs.

* cited by examiner

COMMUNICATION DEVICE FOR PRIMATES, IN PARTICULAR PERSONS, AND METHOD FOR OPERATING SUCH A DEVICE

The invention relates to a communication device for primates, in particular persons, and more in particular patients suffering from dementia. The invention also relates to a method for operating such a communication device.

For people with dementia, the body's functions degenerate as the brain's functions deteriorate. People with severe dementia cannot communicate and are completely dependent on others for their care. Near the end, the person may be in bed most or all of the time, as the body shuts down. The person with dementia will experience increasing problems understanding what is being said to them and what is going on around them. They are likely to find it difficult to communicate with other people. They may gradually lose their speech, or they may repeat a few words or cry out from time to time. However, verbal language is only one way of communicating. The person's expression and body language may give clues about how they are feeling. Many people suffering from dementia can still receive and return emotional signals long after they have lost the ability to speak.

A primary object of the invention is to provide a device for facilitating communication between a person suffering from dementia and another person.

A secondary object of the invention is to provide a device for facilitating alternative communication between primates, in particular persons.

At least one of the aforementioned objects can be achieved by providing a communication device according to the preamble, comprising: at least one electrically conductive first surface to be touched by a first primate, at least one electrically conductive second surface to be touched by at least one second primate, and at least primary electronic circuit electrically connecting said first surface and said second, said primary electronic circuit comprising: at least one detection element for measuring at least one resistance value of a secondary electronic circuit formed by at least the primary electronic circuit, a first primate touching said first surface, at least one second primate touching said second surface, and the first primate and the other least second primate touching each other, and at least one output for producing a specific signal representing the specific resistance value detected by said at least one detection element, wherein said control unit is configured to register a resistance pattern formed by the development of the detected resistance value as a function of time, wherein said control unit and/or said at least one output being configured to produce at least one specific signal at least partially based upon said registered resistance pattern. For patients who are suffering from severe dementia the communication device according to the invention may significantly facilitate (alternative) communication between a patient and a family member or caretaker. This alternative communication is based upon the sense of interpersonal touch as an input means to produce a representative output, based upon a detected electrical resistance, observable for both the patient and the family member or caretaker. Hence, the one or multiple output signals represent a translation of the specific manner of (intuitively) performed skin-specific gesture(s). This allows the patient to better express emotions, and also to better express commands relating to interpersonal communication. For many standard commands, conventional single-touch or multi-touch gestures were successfully transferred to representative signals, which demonstrates the wide spectrum of the skin as an input surface, which creates opportunities for newly shared experiences beyond speech. This skin based manner of communicating can also be used in a non-medical environment and does even not necessarily have to be restricted to human beings, but may also be used by other primates, such as apes, or by apes and human beings, for fun or for educational purposes. In the following, the expression "person" may be replaced by the expression "ape". It is also conceivable that the device and method according to the invention are used by other animals, in particular mammals, such as dogs. Commonly the contact between the first person and the second person may either be directly, by means of direct skin-to-skin touch, or indirectly, by means of an intermediate electrically conductive element, such as e.g. a metal pen.

During use of the device according to the invention, a pattern of the development of the detected resistance value is or can be registered as a function of time by the control unit. Based upon this detected resistance pattern, the control unit and/or output can determine a (corresponding) specific output signal, which can be generated (produced) by said output, such that at least one user of the device will be able to observe this signal generated by the output. Thus more complex sequences of behaviour, in particular different gestures, can be recognised by the device and relevant, co-related output can be generated. The total resistance of the two (or more) users, electrically connected in series during use of the device, is dependent both on the individual resistance of each user and on the contact resistance between said users. This contact resistance is strongly dependent on the way of touching each other, wherein different gestures, such as, for example, holding, grabbing, stroking, kneading, tapping, and tickling, lead to different resistance values, and hence, different resistance patterns, which can be measures in the course of time, and which may serve as basis for producing at least one output signal which is—at least partially—based upon the detected resistance patterns. During use, the user(s) will observe that a different way of mutual touching leads to a different output signal, which facilitates a disabled patient to better express emotions and commands to one or more other persons.

The control unit is (pre)programmed with at least one analysis algorithm to transform at least the monitored resistance pattern into information related to at least one signal, and wherein the control unit is configured to control at least one output to generate said at least one signal. The analysis algorithm can be based upon various techniques, and is based upon a self-contained step-by-step set of operations to transform a detected resistance pattern into a specific (distinctive) output signal. More in particular, by using the detected resistance pattern or information related hereto as input for the analysis algorithm, the algorithm instructions describe a computation that, when executed, proceeds through a finite number of well-defined successive states leading to an output signal to be generated (produced) by at least one output. The transition from one state to the next is not necessarily deterministic; some algorithms, known as randomized algorithms, incorporate random input. At least one analysis algorithm is preferably formed by a decision-tree based algorithm. This decision-tree based algorithm is in fact a Boolean ("yes"/"no") based structure, wherein during successive decision steps, yes-no decisions are made, which successively exclude possible output signals until (at least) one output signal to be generated and/or information relating to said at least one output signal is left. The signal related information can either be the signal itself and/or an instruction (command) or other information necessary to generate a specific signal. To this end, the signal related information can, for example, be a filename of an audio file or image file stored in a content database and eventually instructions to play or open said file in order to produce the content via at least one output. The signal related information is commonly stored in an information database, which makes preferably part of an internal memory of the processor. As said, the control unit is preferably configured to control the output to generate at least one output signal, preferably based upon the predefined signal related information, by using at least one signal content database, such as a sound bank and/or image bank. The signal content database is preferably stored on a storage medium, and wherein the primary electronic circuit comprises a reader for reading the content of the signal content database. The storage medium may be a removable storage medium, such as a flash drive or a Secure Digital (SD) card. By using a removable storage medium for storing output signal related content, a user can easily modify and customize the content of the content database.

The primary electronic circuit preferably comprises at least one database with cross-references at least between predefined resistance patterns related information and predefined signal related information, wherein the control unit is configured to compare the monitored pattern with the predefined resistance patterns related information as stored in the database, and to control at least one output to generate at least one predefined signal derived from said database, in case of sufficiently matching between the monitored resistance pattern and at least one predefined pattern. The comparison executed by the control unit to recognize resistance patterns is commonly performed by using an analysis algorithm. To this end, preferably fingerprints, which are commonly formed by a set of hashes, of predefined resistance patterns related information are stored in the database. Sufficiently matching includes both complete match and substantially matching, wherein this latter expression can be related to a minimum threshold of overlap, such as for example at least 75%, 90%, and/or 95%.

In a preferred embodiment, the device comprises at least one detection element for detecting at least one parameter relating to the actual use of the device, preferably the actual motion of the device, and more preferably the actual acceleration of the device. The detection can for example by formed by a motion sensor, such as a accelerometer (gyroscope). This additional information can be used to determine which output signal has to be generated by at least one output. For example, in case of long-term inactivity, the detection element detects a lack of motion during a longer period in time, such as a couple of minutes, which may trigger generation of a specific output signal. In a particular preferred embodiment, the control unit and/or the at least one output are configured to produce at least one specific signal which is based upon the combination of said registered resistance pattern and said at least one detected further parameter. To this end, a more complex analysis algorithm and/or multiple analysis algorithms may be used to determine the output signal to be generated. It is imaginable that the control unit is configured to register a use related pattern formed by the development of the at least one detected parameter as a function of time, wherein said control unit and/or said at least one output being configured to produce at least one specific signal at least partially based upon said registered use related pattern, and preferably a combination of said registered use related pattern and the registered resistance pattern. This enhanced detection and output signal generation will lead to enhanced possibilities to program and use the device.

It is conceivable that the control unit is configured to produce an output signal only in case of exceeding a predefined minimum resistance value, such as typically at least 500 ohm. This will prevent at least partially that the device is used (unintentionally) by a single user, since the resistance of a single user touching both conductive surfaces is commonly lower than said threshold value, typically 500 ohm. It will be obvious that the overall resistance of multiple users connected in series will commonly be larger than the resistance of a single user.

A detection element as such for detecting the resistivity (or alternatively the conductivity) of the secondary electronic circuit formed during use of the communication device according to the invention, is known, and may, for example, be formed by an ammeter, a volt meter an ohm meter and/or a combination thereof. Similarly the changes in resistivity, conductivity, impedance or admittance may be measured as well. Hereto a frequency generator and a frequency measurement and a signal comparing step may be performed as well. Finally a field effect or capacity may be measured as well without departing from the scope of current invention.

Preferably, the primary the electronic circuit comprises at least one control unit connected to both the at least one detection element and the at least one output. The control unit provides the primary circuit, and hence the secondary circuit, intelligence which facilitates operation of the communication device. Commonly, the control unit comprises a processor and a computer memory provided with (embedded) software.

The control unit is commonly configured to control the at least one output in order to force the at least one output to generate at least one specific signal representing the measured resistance (or conductivity) in the secondary circuit once formed. The output may be configured to generate an acoustic signal, which may be a single tone or a more complex sound, such as a tune (melody), music, pre-programmed speech, or generative soundscape. In case of a single tone it is imaginable that the control unit is programmed such that the frequency of the acoustic signal (tone) generated is directly proportional or otherwise related to the resistance detected by the detection element, which allows person to influence the tone frequency by their manner of touching each other. It is also conceivable that the control unit is programmed such that the volume of the acoustic signal generated is directly or inversely proportional or otherwise related to the resistance detected by the detection element. Alternatively, at least one output may be configured to generate a visual signal (such as light, image, video). To this end, the output may be formed e.g. by a lamp and/or a display. Preferably, the control unit is programmed such that the colour of the visual signal generated is dependent on the resistance detected by the detection element. It is also imaginable that the control unit is programmed such that the intensity of the visual signal generated is dependent on the resistance detected by the detection element. It is also imaginable that the control unit is programmed such that a frame-rate of a video generated is dependent on the resistance detected by the detection element. It is also thinkable that the output is configured to generate another signal, such as e.g. a vibration or (self-initiated) movement of the device.

Preferably, the communication device according to the invention functions in an autonomous way, which allows the communication device to be used at any desired location. To this end, it is preferred that the primary electronic circuit comprises at least one power source for powering both the primary electronic circuit and consequently the secondary electronic circuit. The power source is commonly formed by a battery, which may be rechargeable.

The communication device may comprise more than two electrically conductive surfaces, which allows even more than two primates (persons or apes) to simultaneously communicate by the communication according to the invention.

The first surface and/or second surface can be formed by at least one electrically conductive layer. Thus the surfaces can be touched, whereas the rest of the device or at least the layer below the conductive layer is an insulator, such that proper registration of the conductivity or resistance can be performed.

The electrically conductive layer can be at least partially formed by electrically conductive paint, electrically conductive ink, of electrically conductive fabric. Thus a relative cost effective way the electrodes or sensors can be painted on the surface of the device, and various structures, patterns, and boundary edges and shapes can be made efficient and effective.

At least one of the electrically conductive first surface and the electrically conductive second surface can comprise a segmented surface, a geometric and/or an organic pattern, a distinct and/or a fuzzy boundary layer. Commonly each surface comprises at least one electrical track onto which a primate's hand can be positioned. Depending on the needs for the device such as the conductivity of the skin of a specific users group, the device can be easily and readily be modified, serviced and maintained. It is imaginable that at least one electrically conductive surface is applied onto a wearable carrier, such as a wristband, which can be worn by a user. This may facilitate the use of the device, in particular for heavily disable persons.

At least one of the electrically conductive first surface and the electrically conductive second surface can be configured to be touched by a primate's hand. Thus the device is readily understood and used by the users in question. By an easy touch, the device can be used without extensive reading of user manuals, and by the shape of the electrodes the device can be made self-explanatory.

The device preferably comprises an housing accommodating at least a part of the primary electronic circuit, and wherein the at least one electrically conductive layer is applied onto an insulating outer surface of the housing. The housing may be made entirely or partially of an electrically insulating material. The insulating material is preferably wood and/or plastic. Preferably, each conductive layer is partially embedded into the outer surface of the housing. To this end, the outer surface of the housing may be provided with a relief, in particular at least one grooved portion, in which the conductive layers are applied. The conductive layers can be glued onto the outer surface of the housing, preferably by making use of a conductive adhesive, and/or can be clamped by grooves eventually applied in the outer surface of the housing. Each layer is preferably designed such that it substantially fits the hand of a user. Here, each layer preferably has more or less the same shape and dimensioning compared to an average hand.

In a preferred embodiment, the first surface is formed by a first electrically conductive layer and the second surface is formed by a second electrically conductive layer, wherein at least one output is positioned in between the first electrically conductive layer and the second electrically conductive layer. By providing at least output a central location, the output signal(s) produced by said output can be observed by multiple users.

The primary electronic circuit can comprise at least one control unit connected to both the at least one detection element and the at least one output, said control unit being programmed to register changes in the conductivity and/or the resistance of the secondary electronic circuit. Thus the measurement of the behaviour of the users can be registered and a relevant feedback can be presented to them.

The registered changes can be compared with at least one counter in order to recognise repetition in conductivity or resistance. Thus repetitive motions such as tapping or tickling can be registered and relevant feedback can be presented to the users.

A threshold value can be determined, based upon a calibrating sequence. By determining a threshold, background noise can be discriminated from the actual behaviour of the users.

Variations in conductivity or resistance of the secondary circuit can be compared with various counters and thresholds, in order to detect repetition of touch, intensity of touch, entry or exit of touch.

The device can be a portable device, in particular handheld device. Thus advanced communication can be brought e.g. to patients in remote areas, or in places where utilities supply is interrupted or not available.

The invention also relates to a method for operating a communication device according to any of the foregoing claims, comprising the steps of: allowing a first primate to touch the electrically conductive first surface of the communication device, allowing at least one second primate to touch at least one electrically conductive second surface of the communication device, allowing the first primate and the at least one second primate to make mutual electrical contact, in particular by touching each other, to form a secondary electronic circuit, and generating a specific signal by the output of the communication device dependent on a specific resistance value detected by said at least one detection element of the communication device upon formation of the secondary electronic circuit. This method allows an enhanced communication between the users of the device.

The signal generated in the last step of the above described method can comprise an acoustic, a tactile, a tangible, an olfactory, a gustative, a visible, and/or pallesthesian signal. Thus users with various or different impairments in their senses can still communicate.

In the method, a calibration step can be performed beforehand. This can assist in filtering out any background noise. This calibration step can comprise the steps of: the first primate and the second primate each touch one of the sensors on the device, the relevant signal is registered, a first noise threshold is calculated based on the noise level registered in the second step; the first primate and the second primate are requested to firmly touch each other e.g. by firmly holding each other's hand, a second continuous touch level is calculated on the basis of the measured resistivity or conductivity of the secondary circuit comprising the two touching primates, the calibration step is finalised by a signal, indicating the primates that the device is ready for use. In this method, the first and/or the second primate can be a human being, unable to communicate otherwise, wherein the disability to communicate can originate e.g. from any mental or geriatric disease, including Alzheimer's disease, senility, Korsakov's syndrome and or any other communication imparting diseases.

Alternatively, the first and second primate can have a mutual interaction due to or in relation to sport training, leisure, gaming, fighting skills, sexual intercourse, where touch related communication can give an extra educative or pleasure stimulus. Thus another dimension can be provided to various human-human, or human-pet or other inter or intra creature interactions can be enhanced.

Preferred embodiments of the invention are indicated in the following clauses:

1. Communication device for primates, in particular persons, comprising:
   at least one electrically conductive first surface to be touched by a first primate,
   at least one electrically conductive second surface to be touched by at least one second primate, and
   at least primary electronic circuit electrically connecting said first surface and said second, said primary electronic circuit comprising:
   at least one detection element for measuring at least one resistance value of a secondary electronic circuit formed by at least the primary electronic circuit, a first primate touching said first surface, at least one second primate touching said second surface, and the first primate and the other least second primate touching each other, and
   at least one output for producing a specific signal representing the specific resistance value detected by said at least one detection element.

2. Device according to clause 1, wherein the primary the electronic circuit comprises at least one control unit connected to both the at least one detection element and the at least one output.

3. Device according to clause 1 or 2, wherein at least one output is configured to generate an acoustic signal.

4. Device according to clauses 2 and 3, wherein the control unit is programmed such that the frequency of the acoustic signal generated is directly proportional to the resistance detected by the detection element.

5. Device according to clause 2 and clause 3 or 4, wherein the control unit is programmed such that the volume of the acoustic signal generated is directly proportional to the resistance detected by the detection element.

6. Device according to any of the foregoing clauses, wherein at least one output is configured to generate an visual signal.

7. Device according to clauses 2 and 6, wherein the control unit is programmed such that the colour of the visual signal generated is dependent on the resistance detected by the detection element.

8. Device according to clause 2 and clause 6 or 7, wherein the control unit is programmed such that the intensity of the visual signal generated is dependent on the resistance detected by the detection element.

9. Device according to one of the foregoing clauses, wherein the primary electronic circuit comprises at least one power source for powering both the primary electronic circuit and the secondary electronic circuit.

10. Device according to one of the foregoing clauses, wherein the first surface and/or second surface is formed by at least one electrically conductive layer.

11. Device according to clause 10, wherein the electrically conductive layer is at least partially formed by electrically conductive paint.

12. Device according to clause 10 or 11, wherein at least one of the electrically conductive first surface and the electrically conductive second surface comprises a segmented surface, a geometric and/or an organic pattern, a distinct and/or a fuzzy boundary layer.

13. Device according to one of the foregoing clauses, wherein at least one of the electrically conductive first surface and the electrically conductive second surface is configured to be touched by a primate's hand.

14. Device according to one of the foregoing clauses, wherein the primary electronic circuit comprises at least one control unit connected to both the at least one detection element and the at least one output, said control unit being programmed to register changes in the conductivity and/or the resistance of the secondary electronic circuit.

15. Device according to clause 14, wherein the registered changes are compared with at least one counter in order to recognise repetition in conductivity or resistance.

16. Device according to clause 15, wherein a threshold value is determinable, based upon a calibrating sequence.

17. Device according to clause 16, wherein variations in conductivity or resistance of the secondary circuit are compared with various counters and thresholds, in order to detect repetition of touch, intensity of touch, entry or exit of touch.

18. Device according to any of the preceding clauses, wherein a pattern of the development of the detected resistance value is registered as a function of time, and said control unit and/or said at least one output being configured to produce at least one specific signal based upon said registered pattern.

19. Device according to clause 14, wherein the primary electronic circuit comprises at least one database with cross-references between predefined resistance patterns related information and predefined signal related information, wherein the control unit is configured to compare the monitored pattern with the predefined resistance patterns related information and to control at least one output to generate at least one predefined signal derived from said database, in case of sufficiently matching between the monitored pattern and at least one predefined pattern.

20. Device according to one of the foregoing clauses, wherein the device is a portable device, in particular handheld device.

21. Method for operating a communication device according to any of the foregoing clauses, comprising the steps of:
   A) allowing a first primate to touch the electrically conductive first surface of the communication device,
   B) allowing at least one second primate to touch at least one electrically conductive second surface of the communication device,
   C) allowing the first primate and the at least one second primate to make mutual electrical contact, in particular by touching each other, to form a secondary electronic circuit, and
   D) generating a specific signal by the output of the communication device dependent on a specific resistance value detected by said at least one detection element of the communication device upon formation of the secondary electronic circuit.

22. Method according to clause 21, wherein the signal generated in step D) comprises an acoustic, a tactile, a tangible, an olfactory, a gustative, a visible, and/or pallesthesian signal.

23. Method according to clause 21 or 22, wherein a calibration step is performed before step A).

24. Method according to clause 23, wherein the calibration step comprises:
   I) the first primate and the second primate each touch one of the sensors on the device,
   II) the relevant signal is registered, III) a first noise threshold is calculated based on the noise level registered in step II;

IV) the first primate and the second primate are requested to firmly touch each other e.g. by firmly holding each other's hand, V) a second continuous touch level is calculated on the basis of the measured resistivity or conductivity of the secondary circuit comprising the two touching primates, VI) the calibration step is finalized by a signal, indicating the primates that the device is ready for use.

25. Method according to any of clauses 21-24, wherein the first and/or the second primate is a human being, unable to communicate otherwise.

26. Method according to clause 25, wherein the disability to communicate originates from any mental or geriatric disease, including Alzheimer's disease, senility, Korsakov's syndrome and or any other communication imparting diseases.

27. Method according to clause 21-24, wherein the first and second primate have a mutual interaction due to or in relation to sport training, leisure, gaming, fighting skills, sexual intercourse, where touch related communication can give an extra educative or pleasure stimulus.

The present invention will be further elucidated on the basis of the non-limitative exemplary embodiments shown in the following figures.

The figures represent specific exemplary embodiments of the inventions and should not be considered limiting the invention in any way or form. Throughout the description and the figures the same or corresponding reference numerals are used for the same or corresponding elements.

Figure 1:
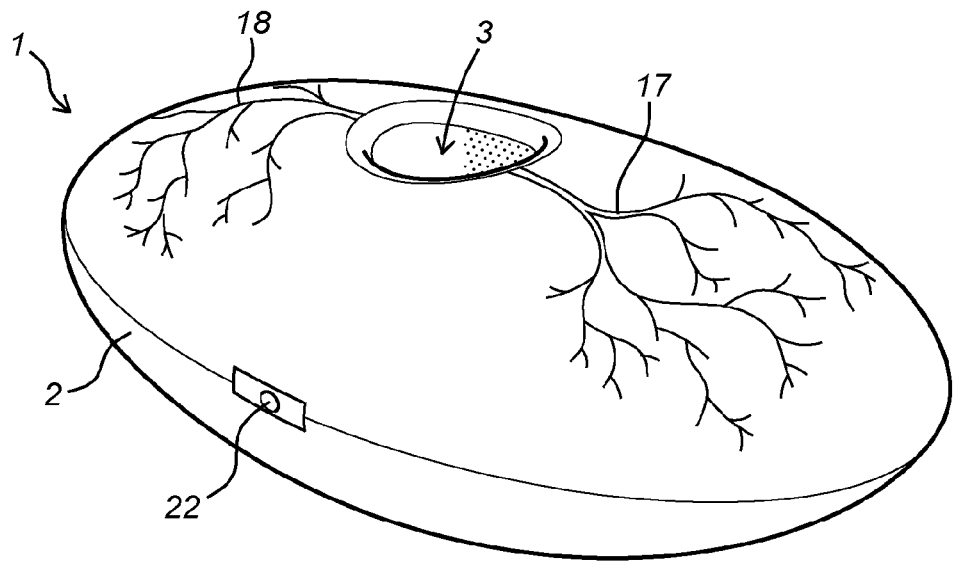
FIG. 1 depicts a schematic perspective view of communication device according to a first embodiment of the invention.

FIG. 1 depicts a first embodiment of the communication device 1. The device 1 is having an ellipsoid body 2, such that it has a friendly appearance, which can be of an advantage by inviting users to touch the device 1. In the ellipsoid body, an opening 3 is positioned, which opens up a channel for a signal exiting the device 1. This signal can be e.g. an acoustic signal or any other suitable signal, such as a visual, tactile, or olfactory signal.

Two sensors 17 and 18 are placed on the surface of the ellipsoid body 2, which are conductive pads or structures, which can come into conductive contact with the skin of the user. In FIG. 1, the two sensors 17 and 18 are structured as trees, where the trees branch of in branches and smaller branches, such that a conductive contact with users is dependent on the positions and amount of surface that is being touched by each user. The conductive sensors can comprise a conductive paint, that is painted on the surface of the device 1, or being a metal or conductive foil, electrically conductive ink, of electrically conductive fabric or any other electrically conductive layer or coating. If conductive paint is used, the paint can comprise metal particles such as copper particles or graphite particles.

The ellipsoid body 2 of the device 1 can be equipped with a power and/or calibration switch 22, which is explained in more detail herein below.

Figure 2:
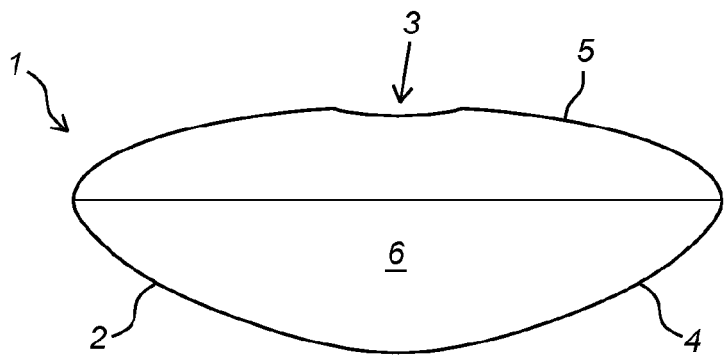
FIG. 2 depict a schematic cross sectional front view of the device according to FIG. 1.
Figure 3:
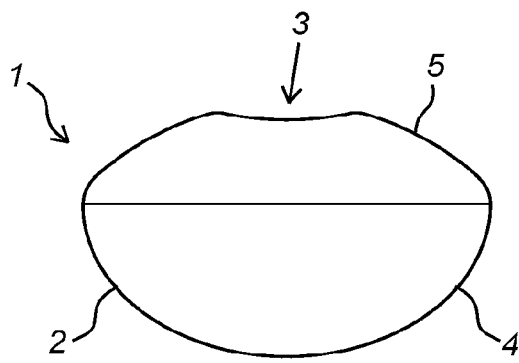
FIG. 3 depicts a schematic cross sectional side view of the device according to FIG. 1.

In FIGS. 2 and 3 schematic cross sectional side views of the device 1 are depicted. In FIG. 2, the ellipsoid body 2 comprises two shell parts, a lower shell part 4 and an upper shell part 5, defining an inner space 6, wherein the electric equipment can be positioned.

The shape of the ellipsoid body 2 is chosen such that it can be represented by e.g. a set of Bézier splines giving the opportunity to differentiate the inclination of every curve in the design of the body 2. For example the upper curved shape of the upper shell part 5 accommodates for a comfortable hand placement, while the lower curved shape of the lower shell part 4 allows for optimal rotation and better holding. Because of the specific shape of the device 1, it can wobble and move on a table in various ways and, if a user touches the device 1, it has a way of moving that is typically different when a second user is touching the device 1 simultaneously. This variation in dynamic behaviour alone can be part of the communication possibilities of the device 1.

Figure 4:
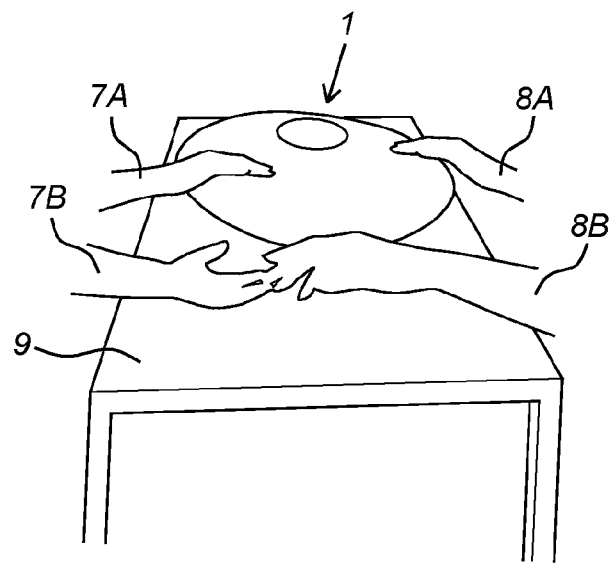
FIG. 4 depicts a first schematic perspective view of the use of the device as depicted in FIG. 1 according to an embodiment of the invention.

In FIG. 4 the use of the device is depicted in a schematic way. Here a first user 7 is touching the device 1 with his or her left hand 7A, while a second user 8 is touching the device 1 with his or her right hand 8A. Both users 7 and 8 touch each other simultaneously with the right hand 7A and left hand 8B respectively. The controller 16 in the inner circuit of the device 1 can, dependent on the resistance in the external circuit between the sensors 17 and 18, and the users 7 and 8, generate one or more signals. In FIG. 4, the device 1 is placed on a table 9 and the users 7 and 8 are both sitting or standing at the table 9.

Figure 5:
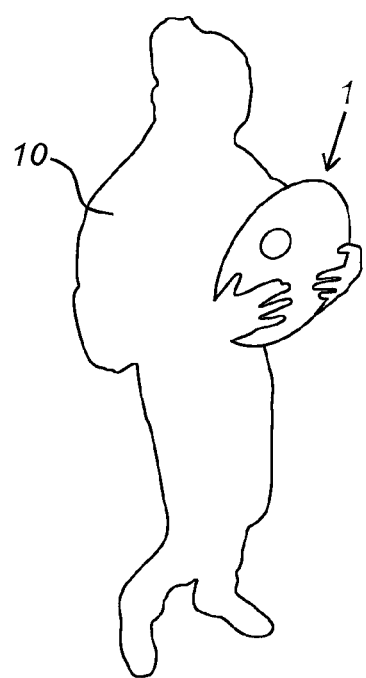
FIG. 5 depicts a schematic perspective view of the use of the device as depicted in FIG. 1 according to another embodiment of the invention.
Figure 6:
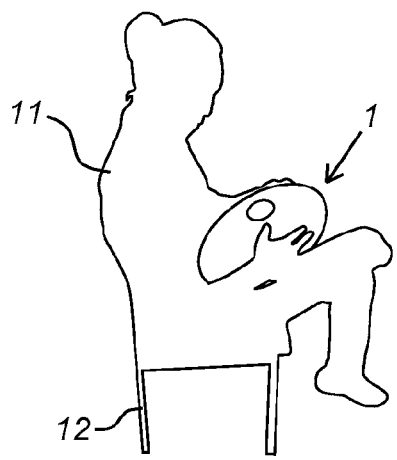
FIG. 6 depicts a schematic perspective view of the use of the device as depicted in FIG. 1 according to yet a further embodiment of the invention.

In an alternative embodiment, as is depicted in FIGS. 5 and 6, the device 1 can be used by a single user 10 or 11 only. Here the user 10 is standing or user 11 is sitting an holding the device 1 with two hands. The tree shaped sensors 17 and 18 can build a conductive circuit with the user touching both the sensors 17 and 18 with both his or her hands. By varying the place of touch, a differentiating response in the form of a signal can be generated by the device 1. This signal can be a sound, varying in pitch, colour and volume depending on the variations in resistance, provided for by the variation is e.g. the hand positions on the device 1, the amounts of contact surface between the hands and the sensors 17 and 18, the conductance of the skin of the user and the amount of pressure the user is exerting on the sensors 17 and 18 of the device 1.

Figure 7:
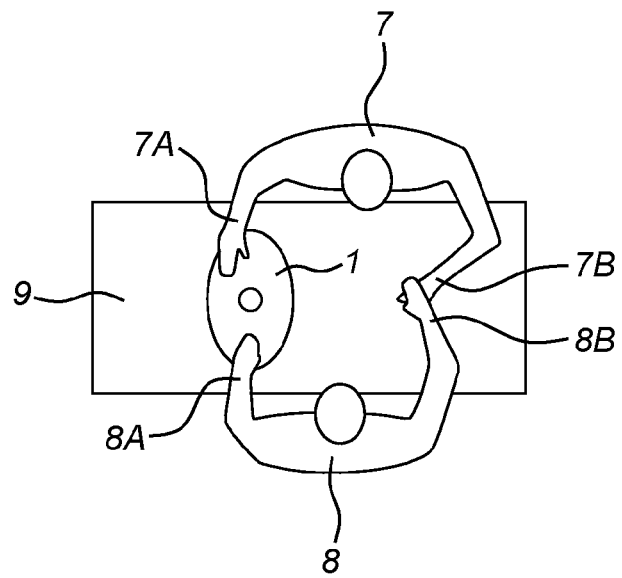
FIG. 7 depicts a schematic top view of the use of the device as depicted in FIG. 1 according to another embodiment of the invention.

FIG. 7 depicts in a schematic top view the use as is depicted in FIG. 4. Both the users 7 and 8 are sitting on opposite sides of a table 9 and are touching the device 1 with hands 7A and 8A and are simultaneously touching each other with hands 7B and 8B. Here, by varying the firmness of the touch, its frequency, the conductivity of both users, and/or the positions of the hands 7A and 8A on the device can give various responses by the device 1. This can be an variation in an acoustic signal, a visual signal, an olfactory signal and/or a combination of these signals.

Figure 8:
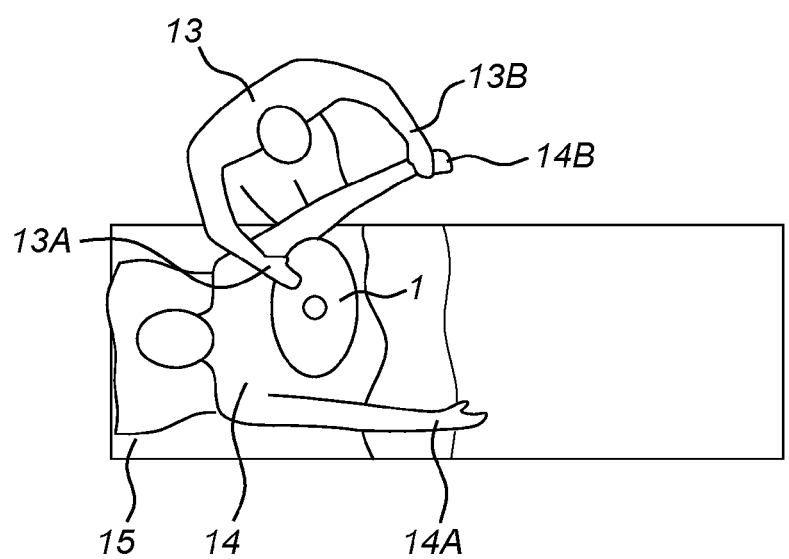
FIG. 8 depicts a schematic top view of the use of the device as depicted in FIG. 1 according to yet a further embodiment of the invention.
Figure 9:
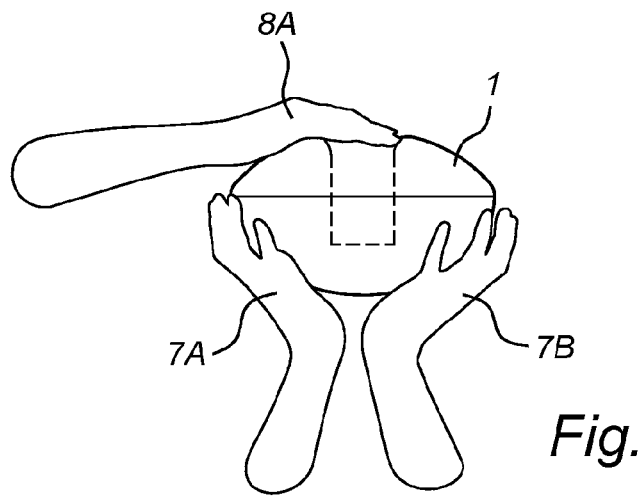
FIG. 9 depicts a schematic top view of the use of the device as depicted in FIG. 1 according to still another embodiment of the invention.
Figure 10:
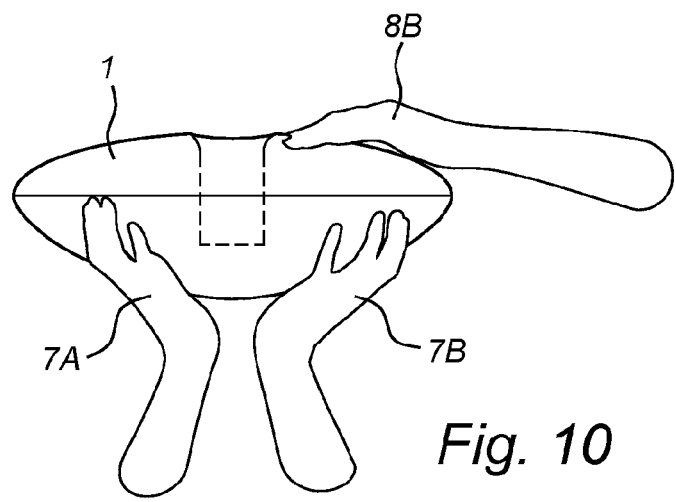
FIG. 10 depicts a schematic top view of the use of the device as depicted in FIG. 1 according to yet a further embodiment of the invention.

In a further embodiment, as is depicted in FIG. 8, one 14 of the two persons 13 and 14 can be a patient being in bed 15. Here the device 1 is resting on the chest of person 14 and he or she is touching with his or her left hand 14B the left hand 13B of person 13, while person 13 is simultaneously touching the device 1 with his or her right hand 13A. FIGS. 9 and 10 depict an alternative situation, where one person 7 is touching the device with both hands 7A and 7B, whereas the other person 8 is touching the device 1 with only one hand 8A or 8B.

Figure 11:
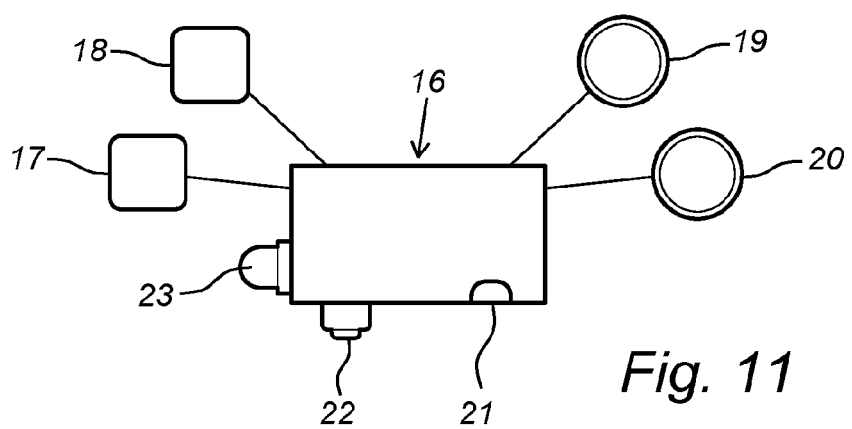
FIG. 11 depicts a schematic view of a circuit with a controller used in the device according to an embodiment of the invention.

In FIG. 11, the electronic circuit of the device 1 is depicted in a schematic view. The circuit comprises a controller 16, to which the sensors 17 and 18 are connected on input connections of controller 16, and outputs 19 and 20 are connected to the output connections of the controller 16. The controlled 16 can be any form of logical device, such as an Arduino or a Raspberry PI as a standard component or any other suitable PLC.

To the controller 16 can be connected to a led 23, to a power and calibration switch 22 and to a charger inlet 21.

Thus a device for generating sensory feedback from interpersonal touch gesture detection is provided, that virtually is an interactive device for generating sensory feedback from measuring a combined resistance of anything and anybody that participates in an electronic circuitry. By this device, different kinds of gestures can be differentiated such as grabbing, holding, padding, stroking, kneading, tapping, tickling. It can be used by humans, but also other primates or animals, in particular mammals, can make use of this device. The gestures can be defined as (combinations of) categories of touch gesture patterns such as: "no touches"; "repetitive touches" and/or "non-repetitive touches"; "intense touches" and/or "mild touches"; "entry gesture" and/or "exit of gesture"; and the repetitiveness in a non-repetitive touches.

The device can be equipped with several methods to recognize which kind of gesture has been performed in the circuitry. Based on the principle of generating sensory feedback from interpersonal touch gesture detection, output can be either one or a combination of sound (audible); texture (tangible), smell (olfactory), taste (gustation); sight (visible); and mechanical oscillations (pallesthesia). The device 1 is developed to allow family members and/or caretakers of e.g. Alzheimer's patients to engage the patients using the sense of touch as the agent. The device thus can create opportunities for newly shared experiences beyond speech. It aims to create a playful and spontaneous environment in which users are open to engage each other and explore the depths of human contact.

Alternative to Alzheimer patients, possible other users could benefit, amongst others potentially included are: caregivers, therapists, geriatrics, patients suffering from mental disorders and/or physical disorders and/or emotional and behavioural disorders and/or functional disorders. Alternatively, the device can be used during sexual contacts, training fight sports, child care, nursery and/or any other human-human interaction.

The device 1 is not necessarily restricted to humans, and can virtually be used by any organism that is able to conduct electrical current. Next to therapeutic applications, the device can also be used for recreational applications that involve physical contact.

The device 1 can be designed as a mobile device and can act as standalone apparatus, without any requirement for external devices or power source in order to operate.

The device 1 can allow anybody or anything, by themselves or as a linked configuration for example, multiple persons that make physical contact, enlarging the electronic circuitry) to interact with it.

The device 1 can include a calibration system that establishes a resistance spectrum within a given predetermined set algorithm to allow for gesture detection distinctions within the spectrum established. To create the spectrum, the calibration system can take the "no touch instance" as one end of the spectrum range and the combined resistance of participators in the circuitry at the other end of the spectrum range. Within any established range, the range as a whole can be divided up in percentage values to establish the gesture detection hierarchy. This calibration can allow for overcoming e.g.: a) differences in skin conductance level (SCL) which can vary depending on the amount of sweat induced moisture on the skin; b) noise threshold, specific bodily fat percentages, age, size of the persons involved etc.

A typical calibration mode can comprise: pressing the switch 22 or an alternative calibration button 5 seconds to initiate a calibration. An first signal, e.g. an audio signal can indicate a start of a calibration mode of the device 1. After several seconds, a second signal, e.g. another audio signal can play, indicating for the users 7, 8, 10, 11, 13 and/or 14 to initiate contact with the device 1 firmly, with e.g. a full palm of the hand. A first, second or other signal, e.g. an audio signal can begin again to indicate that the device 1 is taking data. The contact has to be maintained for the duration of the signal. A further signal e.g. another audio signal can play again to indicate for the users to firmly hold and/or touch each other bare skin, while maintaining their initial contact with the device 1. Another signal can play again to indicate that the device 1 is taking data. At the end of the signal, the calibration is complete and a play or operation mode of the device 1 can begin.

The interpersonal touch gesture detection algorithm system construction can be described as follows: The device 1 measures one, combined resistance of anything and anybody that participates in the circuitry. If there is interpersonal touch gesture changes between somebody who is building up the circuitry, the measured combined resistance changes. The system can have several methods invented to recognize which kind of gesture has been performed in the circuitry. It is elucidated herein below, how this touch gesture pattern recognition is designed. Categories or classifications of touch-gesture-patterns to be recognized can be:

no touches repetitive touches or non-repetitive touches
 intense touches or mild touches
 entry or exit of gesture
 repetitiveness in non-repetitive touches
 no touches First of all, even though there is no connection at all between these measuring electrodes, the measured value is not always equals to zero due to system noise and/or so small portion of the dynamic range should be regarded as a meaningless range and should therefore be rejected as system noise. After removing this system noise, it is aimed for to classify if those touches registered are repetitive or non-repetitive. The repetitiveness can be registered by the system, because it can have at least one or even many internal counters to measure one or more time intervals. At start, the signal is expected to be lower than a noise threshold and this clears out a counter or a counter memory register.

If the signal intensity is higher than the noise threshold, the counter starts to count up until it reaches a predefined value. While the counter is counting but not reaching the predefined maximum value, the gesture is considered as being a repetitive one. If the signal does not go below the noise threshold for predefined number of counts, the count will reach the predefined maximum value, and from that moment the gesture is considered as a non-repetitive one.

If the signal goes below the noise threshold and does not increase again above this threshold, the gesture is considered as being classified a "no touches" again and the counter or its memory register will be cleared and the counter will stop counting up.

If the signal goes below the noise threshold and then becomes higher than the noise threshold again, the counter will restart counting and again, while it is counting and not reaching the maximum, the gesture will be considered as a "repetitive touch".

In this manner, if the signal keep its repetitive character and goes below noise level and returns above the noise level in the predefined time interval, the gesture recognition will change the repetitive character of the touch between a classification as "no touches" and a classification "repetitive touches". In the final stage, the system averages repetitive decisions over certain time interval in order to get a repetitiveness factor of the gesture, after recognizing repetitiveness, we want to classify further if those touches are intense or mild.

Classification of the intensity can be performed as follows: The intensity of a touch just directly follows from the decision if the signal is over certain threshold or not. If the signal is higher than the threshold, then it will be considered as an intense one. Otherwise, it will be considered as a mild one.

When combining or putting this intensity decision and repetitiveness decision together, the system can derive already 4 different cases: mild repetitive gesture (or tapping), intense repetitive gesture (or padding), mild non-repetitive gesture (or stroking) and intense non-repetitive gesture (or holding).

Classification of entering and finishing of gesture can be performed as follows: The system can also detect entry and exit of gesture using another counter. When the classification for a current gesture is updated to something else, use of an edge detection algorithm will classify the entry and exit event of such gesture, a rising edge detection i.e. a "was 0, and now 1" of the gesture classification will detect entry of that gesture for example, grabbing can be considered an entry gesture. Opposite thereto, a falling edge detection "was 1, and now 0" of the gesture classification will detect exit of that gesture. Example of an exit gesture is letting loose or breaking contact.

The sense of repetitiveness depends on the sense of the threshold even though the system made once decision that the gesture is non-repeating, this only means that the signal is repeatedly crossing noise threshold.

Of course, other variable thresholds can be defined to get another sense of a repetitiveness decision.

The classification of repetitiveness in a non-repetitive touches can be performed as follows:

An absolute differentiation of the signal for detecting repetitiveness without a fixed threshold is possible. The system can also differentiate the signal to detect repetitiveness, not against fixed threshold but as a general matter. Thereto, the system can collect a number of counts of instant increase of an absolute differentiated signal that exceeds a certain threshold for certain time interval, this collected number of counts of a viable instant increases can summarize the tendency of waving or undulations in the signal, so, applying a threshold to this number of collected counts timely, the system can recognize an intensity of a waving or undulation aspect of the gesture, for example, kneading is an undulation or waving motion.

Figure 12:
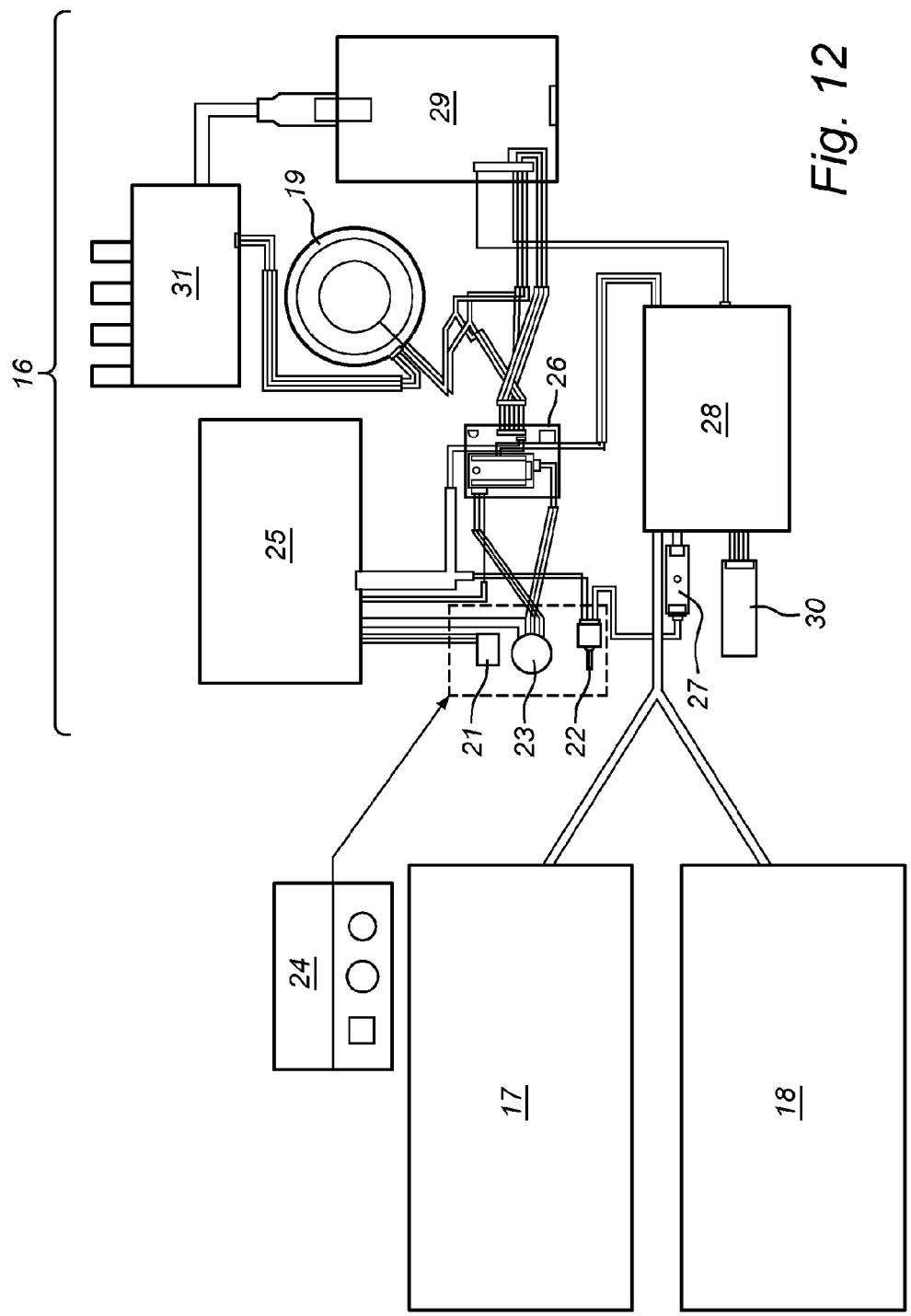
FIG. 12 depicts a schematic view of the electronic components of the device in a further embodiment of the invention.

FIG. 12 represents a schematic view of the various electronic components that may be integrated in the device 1. In this figure the two sensors 17 and 18 are connected to a sensor board 28. The sensor board 28 can be powered through the sensor board charger 27, which can be connected to a mode switch 22. Mode switch 22 can be connected to a battery pack 25 and to charging input or power supply 21. The mode switch is depicted separately, but can be integrated with the connector of the power supply 21. This mode switch 22 can be integrated in a control panel 24, together with the charging input and power supply 21 and the LED 23.

The power requiring electronic components can be connected to a power manager 26, which closely cooperates with the battery pack 25. Through charging input and power supply 21 can the battery be charged, while the power manager can monitor and control the charging of the battery pack 25. At the same time the power control can distribute power to the power consuming elements of the controller 16.

In use, the information collected by the sensors is transferred to the sensor board 28, which processes the information, e.g. is digitalizing the input and is transferring this information to the Programmable logic computer (PLC) 29. This PLC can be any suitable logical circuit such as a Raspberry Pi, an Arduino or the like.

The PLC 29 can be connected to an audio card 31, which is connected to an output 19, which is a speaker. The PLC 29 is further connected to the power manager 26 for its power supply.

In use, the sensors 17 and 18 provide information, which is processed by the sensor board 28, analyzed and further processed by the PLC 29, which on the basis of the input and processing routines as outlined herein above, provides an signal to the audio card 31, which at its turn controls the speaker as output 19.

The invention is not to be considered to be limited to the above description and/or to the figures. For instance the device can be made of wood, stone, plastic, metal, or any other suitable construction material. The device 1 can comprise virtually any shape, including two separate pods, connected with a wire. The device 1 can be provided with external outputs, such as speakers that are in radio contact with the device, such as a Bluetooth protocol.

The sensors 17 and 18 can have various shapes and structures such as pads with a defined boundary, a fuzzy boundary, comprise structured or unstructured patterns, have geometrical or organic shapes etc. etc.

Figure 13:
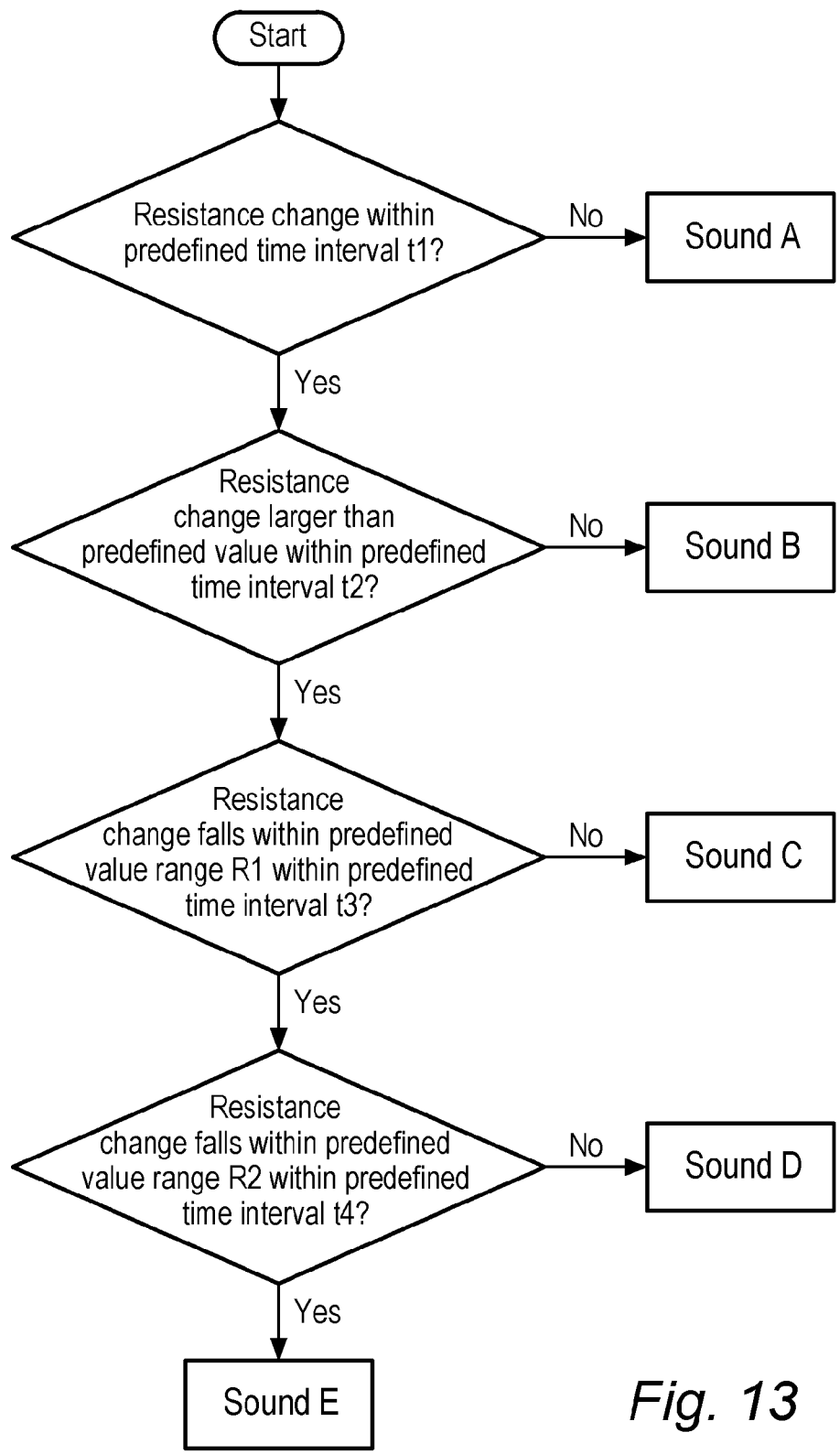
FIG. 13 depicts a decision-tree based analysis algorithm which can be used in the device and method according to the invention.

FIG. 13 depicts a decision-tree based analysis algorithm which can be used in the device and method according to the invention. As can be seen in FIG. 13, during monitoring (measuring) the resistance value in the course of time, and hence a resistance pattern, various successive yes-no decision steps will be run through, thereby leading to an output sound to be generated. The indicated time intervals t1, t2, t3, and t4 may mutually vary. The same applies to the predefined resistance ranges R1,R2. During long-time inactivity, sound A will be produced. In case large resistance changes are detected, sound B will be produced. Sounds C and D will be produced in case of more moderate resistance changes falling within the predefined ranges R1 and R2, and for all other situations sound E will be produced.

FIGS. 14a-14h depict, as an example, a different analysis algorithm which can be used in the device and method according to the invention. During a first step (FIG. 14a), the most common resistance changes as a function of time are plotted in a resistance-time diagram, wherein each typical resistance pattern is plotted in a distinctive diagram. This diagram is commonly a two-dimensional diagram, wherein on the horizontal (X) axis, the time is visualised, and on the vertical (Y) axis, the resistance is visualised. Storing the full pattern in the database will easily occupy an enormous amount of space. To reduce the space for storage, the diagram is transformed in the representation visualised in FIG. 14b. The crosses visualised in FIG. 14b correspond to the peaks of a predefined resistance pattern. In FIGS. 14a-14h an exaggerated resistance pattern is shown to facilitate illustration of this analysis algorithm. The transformed diagram is preferably stored in a predefined pattern database, more preferably such that it is efficient to search for a match (easy to index). To this end, one or more points (crosses) of the diagram are assigned to act as "anchor points" and zones in the vicinity of them are assigned to fall within a "target zone" (see FIG. 14c). Now, for each point in the target zone, they will create a hash that will be the aggregation of the following: the resistance at which the anchor point is located (f1)+the resistance at which the point in the target zone is located (f2)+the time difference between the time when the point in the target zone is located in the pattern (t2) and the time when the anchor point is located in the pattern (t1)+t1. To simplify: hash=(f1+f2+(t2−t1))+t1 (see also FIG. 14c). After this, each hash, and preferably set of co-related hashes representative for a predefined resistance pattern (also referred to as a "fingerprint") is stored in the database.

The manner of comparing a monitored (detected) resistance pattern with the predefined patterns stored in the database is described below. Firstly, during detection of an actual resistance pattern, the same fingerprinting process as described above is executed. Each hash generated from the monitored pattern, will be searched for a match in the database.

If a match is found, one will have the time of the hash from the detected pattern (th1), the time of the hash from the predefined pattern stored in the database (th2) and preferably also implicitly the ID or other information relating to the output signal to be generated. Basically, th1 is the time since the beginning of the detected pattern until the time of the detected pattern hash and th2 is the time since the beginning of the predefined pattern and the time of the predefined pattern hash.

Figure 14A:
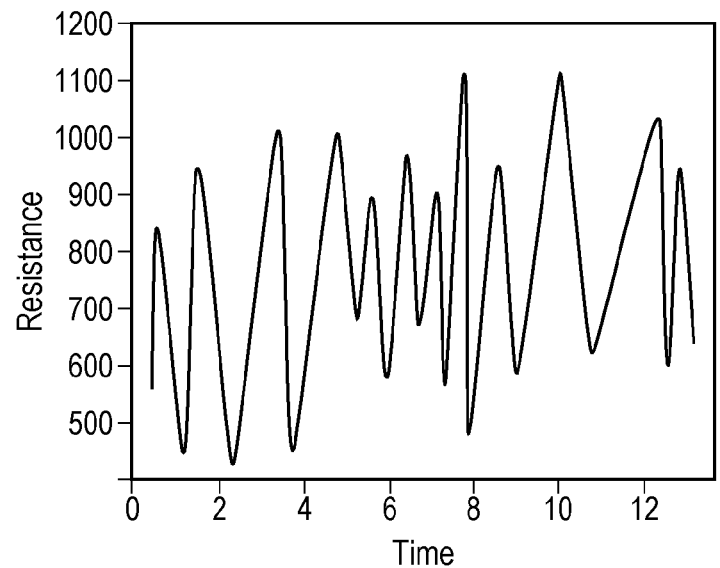
FIGS. 14*a*-14*h* depict a different analysis algorithm which can be used in the device and method according to the invention.
Figure 14B:
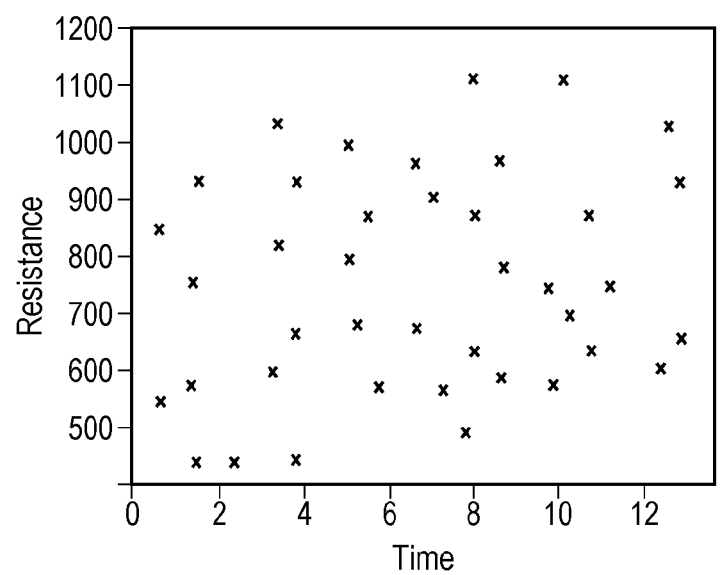
Figure 14C:
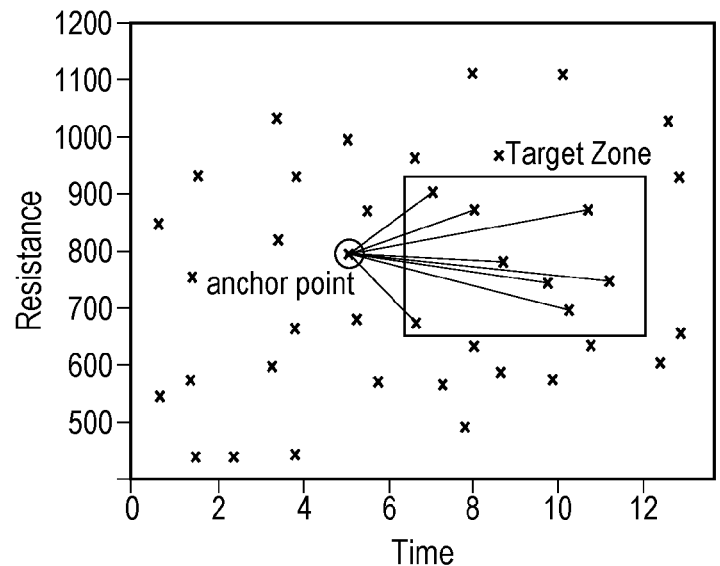
Figure 14D:
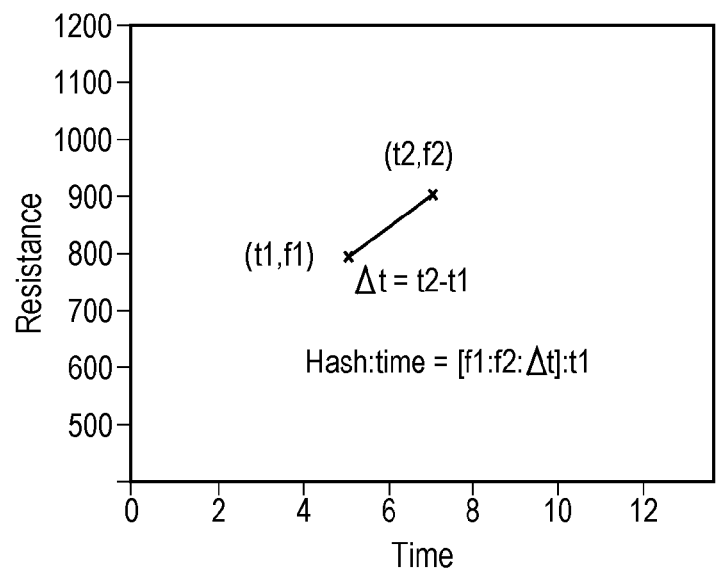
Figure 14E:
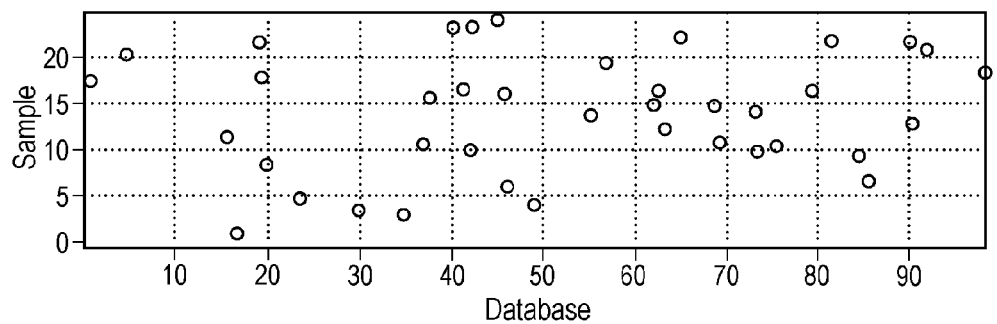
Figure 14F:
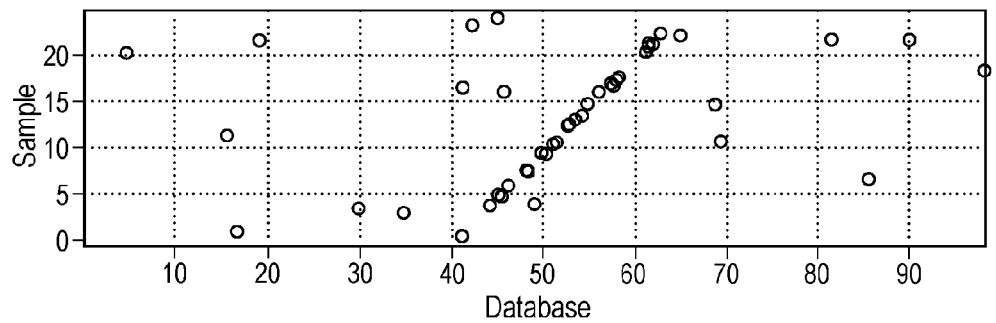

Now, commonly a new graph called a scatter graph will be drawn (FIG. 14e). The graph will have on the horizontal axis (X) the time of the predefined resistance pattern in the database and on the vertical axis (Y) the time of the recorded pattern. On the X axis, th2 is marked, and on the Y axis, th1 is marked. The point of intersection of the two occurrence times (th1 and th2) is marked with a small circle. If the graph will contain a lot of pairs of th1's and th2's from the same pattern, a diagonal line will form (see FIG. 14f). The rate at which the peaks (the small crosses from the simplified chart according to FIG. 14b) in the database appear will be the same rate in which the peaks appear in the recorded pattern. By pairing these times, the coordinates on the scatter graph will grow constantly (to the right-top of the graph) as the time passes on both axes.

Figure 14G:
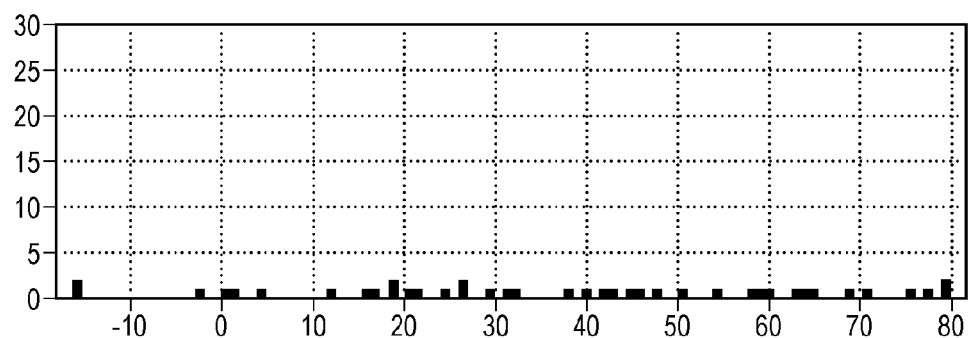
Figure 14H:
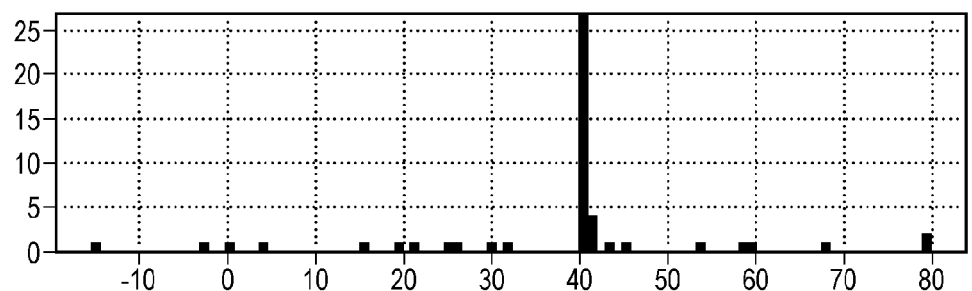

Finally, the difference between th2 and th1 (dth) will be calculated and plotted in a histogram. If there is a match in the graph plotted, then there will be a lot of dths with the same value, because, basically, subtracting the th2 from th1 will give the offset from where the detected pattern was recorded (the difference between a point in the original song and the same point in the recorded sample). This will result in a peak within the histogram, which will confirm a match. FIG. 14g depicts a histogram of a non-matching run, and FIG. 14h depicts a histogram of a matching run. These and other variations and/or modifications are considered within the spirit and scope of the invention and are considered to lie within the skills of the man skilled in the art without him becoming inventive. These variations and modifications are considered part of the framework as outlined in the appended claims.

LIST OF REFERENCE SIGNS

1. Communication device
2. Ellipsoid body
3. Opening
4. Lower shell part
5. Upper shell part
6. Inner space
7. Person
7A. Left hand
7B. Right hand
8. Person
8A. Right hand
8B. Left hand
9. Table
10. Person
11. Person
12. Chair
13. Person
13A. Right hand
13B. Left hand
14. Person
14A. Right hand
14B. Left hand
15. Bed
16. Controller
17. Sensor
18. Sensor
19. Output (speaker)
20. Output (speaker)
21. Charging input
22. Mode switch
23. Output (LED)
24. Control panel
25. Battery pack
26. Power manager
27. Sensor board charger
28. Sensor board
29. Programmable logic computer (PLC)

30. BT Module
31. Audio card

The invention claimed is:

1. Communication device for primates, in particular persons, comprising:
- at least one electrically conductive first surface to be touched by a first primate,
- at least one electrically conductive second surface to be touched by at least one second primate, and
- at least one primary electronic circuit electrically connecting said first surface and said second, said primary electronic circuit comprising:
  - at least one detection element for measuring at least one resistance value of a secondary electronic circuit formed by at least the primary electronic circuit, a first primate touching said first surface, at least one second primate touching said second surface, and the first primate and the other least second primate touching each other,
  - at least one output for producing a specific signal representing the specific resistance value detected by said at least one detection element, and at least one control unit connected to both the at least one detection element and the at least one output, wherein at least one output is configured to generate an acoustic signal, wherein said control unit is configured to register a resistance pattern formed by the development of the detected resistance value as a function of time, wherein said control unit and/or said at least one output being configured to produce at least one specific signal at least partially based upon said registered resistance pattern, by using at least one signal content database, wherein at least one signal content database is a sound database, and wherein the primary electronic circuit comprises at least one database with cross-references at least between predefined resistance patterns related information and predefined signal related information, wherein the control unit is configured to compare the monitored pattern with the predefined resistance patterns related information as stored in the database, and to control at least one output to generate at least one predefined acoustic signal derived from said sound database, in case of sufficiently matching between the monitored resistance pattern and at least one predefined pattern.

2. Device according to claim 1, wherein the control unit is programmed with at least one analysis algorithm to transform at least the monitored resistance pattern into information related to at least one signal, and wherein the control unit is configured to control at least one output to generate said at least one signal.

3. Device according to claim 2, wherein said analysis algorithm is formed by a decision-tree based algorithm.

4. Device according to claim 2, wherein at least a part of the signal related information is stored in a database, which makes part of an internal memory of the processor.

5. Device according to claim 1, wherein the signal content database is stored on a storage medium, and wherein the primary electronic circuit comprises a reader for reading the content of the signal content database.

6. Device according to claim 5, wherein the signal content database is stored on a removable storage medium, such as a flash drive or a Secure Digital (SD) card.

7. Device according to claim 1, wherein fingerprints, formed by a set of hashes, of predefined resistance patterns related information are stored in the database.

8. Device according to claim 1, wherein the device comprises at least one detection element for detecting at least one parameter relating to the actual use of the device, the actual motion of the device, and the actual acceleration of the device.

9. Device according to claim 8, wherein the control unit and/or the at least one output are configured to produce at least one specific signal which is based upon the combination of said registered resistance pattern and said at least one detected further parameter.

10. Device according to claim 9, wherein the control unit is configured to register a use related pattern formed by the development of the at least one detected parameter as a function of time, wherein said control unit and/or said at least one output being configured to produce at least one specific signal at least partially based upon said registered use related pattern, and a combination of said registered use related pattern and the registered resistance pattern.

11. Device according to claim 1, wherein the control unit is programmed such that the volume of the acoustic signal generated is related to the resistance detected by the detection element.

12. Device according to claim 1, wherein at least one output is configured to generate a visual signal, wherein the control unit is programmed such that the colour and/or intensity of the visual signal generated is dependent on the resistance detected by the detection element.

13. Device according to claim 1, wherein the first surface and/or second surface is formed by at least one electrically conductive layer, wherein the electrically conductive layer is at least partially formed by electrically conductive paint.

14. Device according to claim 13, wherein at least one of the electrically conductive first surface and the electrically conductive second surface comprises a segmented surface, a geometric and/or an organic pattern, a distinct and/or a fuzzy boundary layer.

15. Device according to claim 1, wherein the primary electronic circuit comprises at least one control unit connected to both the at least one detection element and the at least one output, said control unit being programmed to register changes in the conductivity and/or the resistance of the secondary electronic circuit, and wherein the registered changes are compared with at least one counter in order to recognise repetition in conductivity or resistance, and wherein a threshold value is determinable, based upon a calibrating sequence, wherein, variations in conductivity or resistance of the secondary circuit are compared with various counters and thresholds, in order to detect repetition of touch, intensity of touch, entry or exit of touch.

16. Device according to claim 1, wherein the device is a hand-held device.

17. Method for operating a communication device according to claim 1, comprising the steps of:
- A) allowing a first primate to touch the electrically conductive first surface of the communication device,
- B) allowing at least one second primate to touch at least one electrically conductive second surface of the communication device,
- C) allowing the first primate and the at least one second primate to make mutual electrical contact, in particular by touching each other, to form a secondary electronic circuit, and
- D) generating a specific signal by the output of the communication device dependent on a specific resistance value detected by said at least one detection element of the communication device upon formation of the secondary electronic circuit.

18. Method according to claim 17, wherein the signal generated in step D) comprises an acoustic, a tactile, a tangible, an olfactory, a gustative, a visible, and/or pallesthesian signal.

19. Method according to claim 17, wherein a calibration step is performed before step A), wherein the calibration step comprises:
   I) the first primate and the second primate each touch one of the sensors on the device,
   II) the relevant signal is registered,
   III) a first noise threshold is calculated based on the noise level registered in step II;
   IV) the first primate and the second primate are requested to firmly touch each other e.g. by firmly holding each other's hand,
   V) a second continuous touch level is calculated on the basis of the measured resistivity or conductivity of the secondary circuit comprising the two touching primates, and
   VI) the calibration step is finalised by a signal, indicating the primates that the device is ready for use.

20. Method according to claim 17, wherein the first and/or the second primate is a human being, unable to communicate otherwise, wherein the disability to communicate originates from any mental or geriatric disease, including Alzheimer's disease, senility, Korsakov's syndrome and or any other communication imparting diseases.

\* \* \* \* \*